United States Patent [19]

Konno et al.

[11] Patent Number: 5,308,618
[45] Date of Patent: May 3, 1994

[54] DIETARY FIBER EXTRACTED FROM WHEAT BRAN PHARMACEUTICAL AND DIETARY COMPOSITIONS CONTAINING SAME

[75] Inventors: Tsutomu Konno, Tokyo; Kiro Asano, Inashiki; Takuji Hosoi, Kawasaki, all of Japan

[73] Assignee: Kureha Kagaku Kogyo Kaubushiki Kaisha, Tokyo, Japan

[21] Appl. No.: 874,224

[22] Filed: Apr. 27, 1992

Related U.S. Application Data

[63] Continuation of Ser. No. 694,205, May 3, 1991, abandoned.

[30] Foreign Application Priority Data

May 15, 1990 [JP] Japan ................................. 2-124853
Mar. 15, 1991 [JP] Japan ................................. 3-75731

[51] Int. Cl.$^5$ .................. A61K 35/78; A61K 31/715; A23L 1/168; C07H 1/06
[52] U.S. Cl. .................. 424/195.1; 426/543; 426/618; 514/54; 514/57; 536/128
[58] Field of Search .............. 424/195.1; 514/783, 514/54, 57; 426/542, 543, 618; 536/123, 128

[56] References Cited

U.S. PATENT DOCUMENTS

| | | | |
|---|---|---|---|
| 1,756,574 | 4/1930 | Takamine | 424/195.1 |
| 2,229,684 | 1/1941 | Supplee | 424/195.1 |
| 4,202,885 | 5/1980 | Asano et al. | 424/95 |
| 4,762,825 | 8/1988 | Takeo | 514/54 |

FOREIGN PATENT DOCUMENTS

| | | |
|---|---|---|
| 0025123 | 3/1981 | European Pat. Off. . |
| 0172559 | 2/1986 | European Pat. Off. . |
| 2335235 | 7/1977 | France . |
| 01-62303 | 3/1989 | Japan ................ 424/195.1 |

OTHER PUBLICATIONS

Patent Abstract of Japan, vol. 12, No. 438 (C–544)(3285), Nov. 7, 1988; and JP-A-63165325 (Snow Brand Milk Prod. Co. Ltd.) Jul. 8, 1988).

Database WPIL/Derwent, accession No. 86-018080(03), 1986, Derwent Publications Ltd., London, GB; and JP-A-60241860 (T. Shiota), (Nov. 30, 1985).

*Primary Examiner*—Michael G. Wityshyn
*Assistant Examiner*—Ralph Gitomer
*Attorney, Agent, or Firm*—Nixon & Vanderhye

[57] ABSTRACT

Dietary fiber, obtained from extracting wheat bran with water, having an average molecular weight of $5 \times 10^2$ to $1 \times 10^5$, from 95.3 to 99.0% by weight of a sugar, primarily glucose, and 0.1 to 3.0% by weight protein components. The fiber, when eaten, promotes the digestion and absorption of nutrients, waste excretion and proliferation of *Lactobacillus bifidus* in the large intestine.

5 Claims, 1 Drawing Sheet

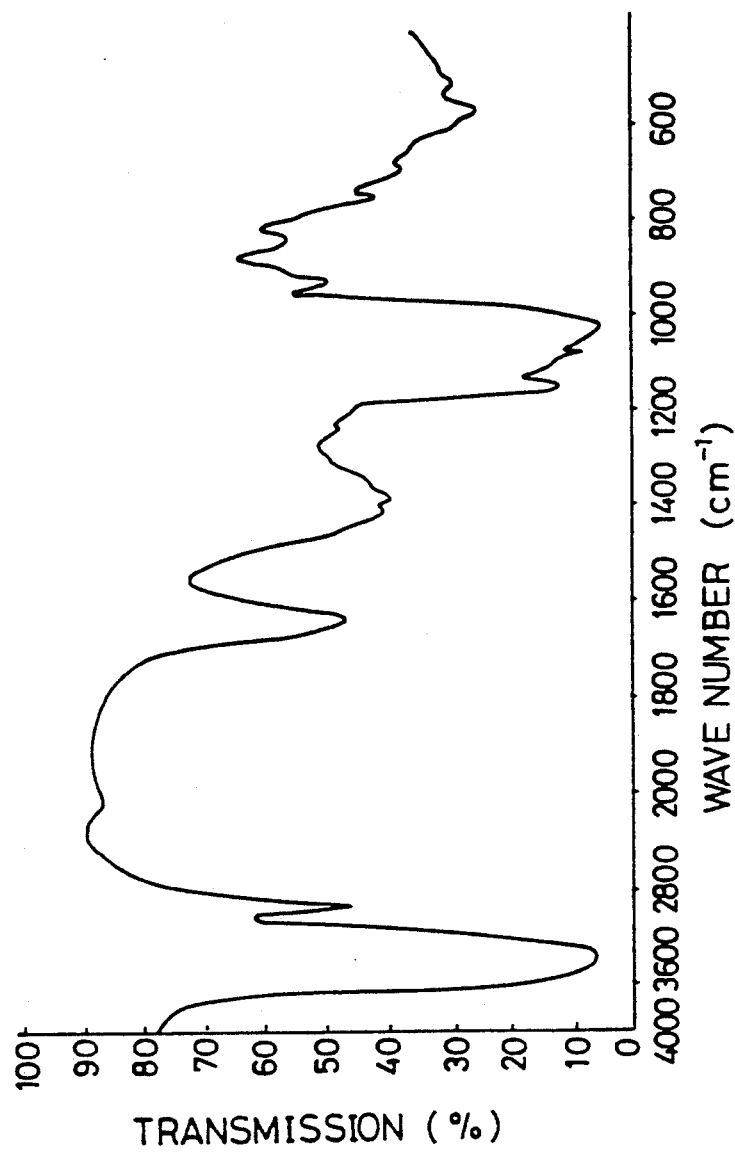

DIETARY FIBER EXTRACTED FROM WHEAT BRAN PHARMACEUTICAL AND DIETARY COMPOSITIONS CONTAINING SAME

This is a continuation of application Ser. No. 07/694,205 filed May 3, 1991, now abandoned.

BACKGROUND OF THE INVENTION

The present invention relates to dietary fiber which can be obtained by extracting bran with an aqueous solvent at a high temperature and differs from a conventional extract of bran with an aqueous solvent in chemical composition and physiological activity; its production; and a physiologically active composition which contains the dietary fiber as an active ingredient.

It has been known that some dietary fibers can be obtained through extraction of bran with an aqueous solvent, but a low yield of the fibers obtainable by this conventional extraction method and a low physiological activity of the fibers have been problems.

F/r instance, Japanese Patent Application Laid-Open (KOKAI) No. 63-165,325 (1988) discloses an extraction of degreased by-products, obtained in a polishing process of grain, such as rice bran, wheat bran or corn husk, with an aqueous solution of sodium hydroxide at room temperature. By the extraction, only 4 g of hemicellulose (B) was obtained from 100 g of rice bran. Accordingly, 4he yield is extremely low and further, because of the extraction with an aqueous solution of NaOH, troublesome steps, such as neutralization and desalting, are necessary to purify the extract.

Japanese Patent Application Laid-Open (KOKAI), No. 64-62,303 (1989) discloses a method to extract husks of grain or beans or a cellulose obtained from the husks with hot water at a temperature of 130° to 160° C. and to purify the extracts, but only a hemicellulose can be obtained by the method. This reference also discloses that when a husk of grain such as bran is extracted at a temperature not lower than 160° C., decomposition of the extract increases accompanied with darkening of its color and low yield of useful substance is induced. Further, a substance extracted at a temperature up to 160° C. gives some deposition of hemicellulose during the purification step.

The present inventors have continuously studied to obtain a useful and physiologically active substance from natural sources. For instance, they have obtained by an extraction of Basidiomycetes with an aqueous solvent an anti-tumor substance having high molecular weight. [refer to Japanese Patent Publication, 56-28, 152 (1981)]. Based on these experiences, they obtained practically indigestible dietary fibers, which is a recent topic as a so-called functional foodstuff, in a high yield. As a result, they have found that a dietary fiber is obtained in a high yield if bran is extracted by an aqueous solvent at a temperature as high as 170° to 220° C., contrary to common knowledge to those skilled in the art.

Further surprisingly enough, they found that in addition to the dietary fiber's physiological activity, such as promotion of digestion and absorption of nutrients and excretion of waste and proliferation of Lactobacillus bifidus within the large intestine, this unique fiber possesses very useful physiological activities, such as anti-tumor, immunological and cholesterol metabolism improving activities.

Based on these findings they have achieved the present invention.

BRIEF EXPLANATION OF THE DRAWING

FIG. 1 illustrates an infrared absorption spectrum of sample 2 obtained from Example 1.

SUMMARY OF THE INVENTION

An object of the present invention is to provide a dietary fiber which can be obtained by extracting bran with an aqueous solvent at a high temperature.

Further, an object of the present invention is to provide a dietary fiber having antitumor, cholesterol metabolism improving and immunological activities in addition to usual physiological activities of dietary fiber and a physiologically active composition which contains the fiber as an active ingredient.

Still further, an object of the present invention is to provide a method to produce a dietary fiber by extracting bran at a high temperature such as 170° to 220° C.

DETAILED DESCRIPTION OF THE INVENTION

The term "bran" in the present invention means whole by-products of processing grain which previously has been mainly used as a feed for livestock. As representative grain, wheat, barley, rice and corn can be exemplified and rye and oat are also included.

The "dietary fiber" in the present invention means the polysaccharides which remain unaltered, neither digested nor absorbed, in the digestive tract and excreted in the original state.

The dietary fiber of the present invention (hereinafter referred to as "the present substance") can be obtained by extracting bran with an aqueous solvent and has following properties:

(a) The average molecular weight determined by the GPC (gel permeation chromatography)-Lalls method is $5 \times 10^2$ to $1 \times 10^5$, preferably $5 \times 10^3$ to $5 \times 10^4$.

(b) It has peaks around 3300 cm$^{-1}$ and 1650 cm$^{-1}$ in an infrared absorption spectrum.

(c) The specific rotation is $$[\alpha]_D^{25} = +138° \text{ to } +145° \text{ (c=0.25, H}_2\text{O)}.$$

(d) The sugar content determined by a color reaction of phenol-sulfuric acid method is 95.3 to 99.0% by weight and the protein content determined by a color reaction of Lowry-F/lin method is 0.1 to 3.0% by weight.

(e) The elementary analysis indicates 35.3 to 39.3% carbon, 4.2 to 6.5% hydrogen and 0.05 to 0.9% nitrogen, all by weight.

(f) It is highly soluble in water, and practically insoluble soluble in chloroform, benzene, ethanol and ether.

(g) It has no clear melting point and starts to decompose, to become black and to carbonize gradually at a temperature around 250° C.

(h) The sugar component comprises at least glucose, xylose and galactose, preferably contains 88 mol % or more glucose, and more preferably contains 88.2 to 95.4 mol % glucose, 3.7 to 7.7 mol % xylose, 0.1 to 1.2 mol % galactose, 1.0 mol % or less fructose and 1.1 mol % or less arabinose.

(i)
The composite amino acids comprise at least aspartic acid, threonine, serine, glutamic acid, proline, glycine, alanine, cysteine, valine, isoleucine, leucine, tyrosine, phenylalanine, hydroxylysine, lysine, histidine and arginine.

Further, the mol % of individual amino acids is preferably in the following range, all in mol %: aspartic acid, 1.8 to 4.8; threonine, 2.4 to 4.0; serine, 6.0 to 8.7; glutamic acid, 27.1 to 33.0; proline, 9.3 to 12.8; glycine, 12.7 to 14.6; alanine, 6.6 to 8.8; cysteine, 0.1 to 0.3; valine, 3.7 to 5.8; isoleucine, 2.5 to 4.2; leucine, 4.4 to 5.8; tyrosine, 1.2 to 2.5; phenylalanine, 3.4 to 4.8; hydroxylysine, 0.9 to 2.5; lysine, 1.3 to 2.4; histidine, 0.9 to 1.9; and arginine, 0.3 to 1.8.

(j) The molar ratio between $\alpha$- and $\beta$-bound glucoses in the glucose component is 1:40 to 1:80.

(k) The molar concentration of 1,4-glucose bond is 85 to 90% and that of 1,3-glucose bond is 4 to 10%.

(l) The molar concentration ratios of methylated sugar obtained by a hydrolysis of the present substance are in the following range:

|  | Ratio |
| --- | --- |
| 2,3,4 6-Tetramethylglucose | 1.0 |
| 2,4,6-Trimethylglucose | 0.55 to 0.93 |
| 2,3,6-Trimethylglucose | 7.96 to 17.94 |
| 2,6-Dimethylglucose | 0.12 to 0.33 |
| 3,6-Dimethylglucose; and | 0.03 to 0.11 |
| 2,3-Dimethylglucose | 0.48 to 0.70 |

(m) The analytical result of the present substance by the Southgate method is as follows:

|  | % by weight |
| --- | --- |
| Water-soluble and hardly digestible polysaccharides | 78 to 96 |
| Cellulose | 1.0 to 5.7 |
| Hemicellulose | 1.7 to 15 |
| Lignin | 1.3 to 3.3 |

The Southgate method is a quantitative analytical method of determining total dietary fiber content and in addition to cellulose, hemicellulose and lignin which are components of the cell wall, macromolecules such as water-soluble and hardly digestible polysaccharides can be determined [see "Determination of Carbohydrates in F//ds. II. Unavailable Carbohydrates", J. Sci. F//d Agric., 20, 331 (1969)].

Description will be made now for the production method of the present substance, which is a part of the present invention. It is a method for obtaining dietary fiber of the present invention in a high yield by extracting bran, a starting material, with an aqueous solvent at 170° to 220° C. or preferably at 180° to 200° C. The extraction time can be adjusted appropriately in accordance with the thermal condition described above, but generally it is preferably 5 to 60 minutes and more preferably 10 to 30 minutes. If the temperature is lower than 170° C. or if the time is less than 5 minutes even when the temperature is maintained not lower than 170° C., the extraction does not proceed sufficiently. If the temperature is higher than 220° C., or if the time exceeds 60 minutes even when the temperature is maintained not higher than 220° C., the extracted substance suffers from decomposition.

This extraction process can be repeated a number of times if the conditions are maintained in the range as specified above.

The aqueous solvent in the present invention is at least one selected from the group consisting of water, water-soluble organic solvents, and aqueous solutions containing a small amount of acid or base. The concentration of the aqueous solution containing a small amount of acid or base should be determined in accordance with the kind of acid or base, but generally an aqueous solution having a concentration of 10% by weight or less can preferably be used. As an organic solvent, methanol, ethanol, isopropyl alcohol, and a like, as an acid, hydrochloric acid, sulfuric acid, acetic acid, and a like and as a base, ammonia, sodium hydroxide, potassium hydroxide, sodium carbonate and a like can be exemplified.

Among these aqueous solvents, water is most preferable when the effect of the solvent on quality of the extracted substance and difficulty involved in purifying the extract are taken into consideration.

The extracted solution, after removing insoluble substances, is neutralized and purified when necessary. A purification of the extracted solution is to remove low molecular weight substances with at least one method selected from the group consisting of salting-out, dialysis, ultrafiltration, reverse osmosis, gel filtration and precipitation by an organic solvent. The molecular weight of the low molecular weight substances to be removed varies according to the type of bran used, extraction conditions, kind of the aquious solvent and necessary quality of the product, therefore it can not be determined simply. However, when wheat bran and water is used as a material and an aqueous solvent, substances having a molecular weight not higher than 400 are preferably removed because it avoids decoloration and deodorization of the present substance.

The dietary fiber after extraction or purification can be used as a solution or a solid after being dried. Besides, water soluble and hardly digestible polysaccharides can be isolated and used singly. The water soluble and hardly digestible polysaccharides in the present invention means substances determined by the Southgate method which will be described in detail later in an Example.

The bran, a raw material, can be extracted as it is, but it may also be treated chemically, enzymatically or physically prior to the extraction in order to facilitate extraction of a specific component of the bran.

Further, the present substance has the following physiological activities.

1. Antitumor Activity

When the present substance is injected intraperitoneally to the Sarcoma-180 transplanted mouse, the inhibition of tumor growth is 50% or more.

2. Proliferation Activity of *Lactobacillus Bifidus*

When the present substance is administered orally to a mouse, the proliferation ratio of *Lactobacillus bifidus* in its feces is 10 fold or more than that of the control.

3. Activity Reducing an Accumulation of Cholesterol

When the present substance is administered orally to a mouse suffering from hypercholesterolemia, the cholesterol level in blood is reduced by about 20% and the level in the liver, by about 30%.

4. Activity Stimulating Immunologic Response

The present substance was added together with phytohemagglutinin and chlorambucil to monocytes obtained from human peripheral blood and the effect of the present substance on the lymphocytes was studied based on uptake of $^3$H-tymidine by the lymphocytes. The present substance significantly improves activity of the lymphocytes which has been suppressed by chlorambucil.

5. Acute Toxicity with a Large D/se of the Present Substance

The present substance was administered orally at a dose of 5 g/kg of body weight to a mouse, and its toxicity was studied. Weight reduction was not observed as compared with the control group and no death occurred. From the above, it is expected that the $LD_{50}$ as the oral administration acute toxicity of the present substance is larger than 5,000 mg/kg of body weight.

The methods used for determining above activities and their results will be described in detail in Examples 3 to 8.

As is obvious from the above, the present substance has not only a remarkably low toxicity but also possesses a variety of useful physiological activities. Accordingly, as is described below, the present substance is beneficial if it is used as an ingredient of a pharmaceutical composition and a dietary composition.

As a pharmaceutical composition, it can be used, judging from the activities described before, as an antitumor drug, growth-stimulants of *Lactobacillus bifidus* in the intestine, a cholesterol metabolism improving agent and a stimulant of immunological reaction. In these pharmaceutical composition, the present substance can be administered orally or parenterally. It can also be used in any conventional dosage form, such as syrup, pill, powder, granule, tablet, capsule, suppository, cream, ointment or spray. In these drug forms, it can be used alone or together with bases such as activators, bonding agents, disintegrating agents, lustering agents, coloring agents or fillers.

The present substance can be used, making better use of the above activities, as a dietary composition having anti-tumor activity, growth stimulating activity of *Lactobacillus bifidus*, cholesterol metabolism improving activity and/or immunology enhancing activity.

The dietary composition, for example, includes salted bean paste (miso), soy bean curd (tofu), retort foods, frozen foods, bread, pie, confections stuffed with sweetened bean paste, fish meat product such as salted, ground and whitened fish meat (kamaboko), baked, ground fish meat (chikuwa), meat products such as hamburger, meat balls, etc., powdered soup, powdered fat, powdered extract, powdered seasonings, powdered sweeteners, candies, drops, boiled and salted kelp (tsukudani), grated cheese, sauce, ketchup, dressing, mayonaise, sauce for grilled meat, biscuits, cookies, wheat noodles (udon), buckwheat noodles (soba) cream, spread, baked and dried rice cake (okaki), baked rice cake (senbei), and so on. The present substance can also be added to general foodstuffs other than listed above in order to give them its unique properties.

The present substance, as a component of a pharmaceutical composition or a dietary composition, can be used as a prophylaxis or a treating agent for the diseases described above. When used as a component of a pharmaceutical composition, it can be administered in a conventional dosage form preferably at a dosage of 0.01 mg/kg body weight to 1,000 mg/kg body weight and more preferably at a dosage of 0.1 to 500 mg/kg body weight, once to several times daily. When used as a dietary composition, it can be given by itself or as a component of a foodstuff or beverage generally at a preferable dosage of 0.01 to 10,000 mg/kg body weight and at more preferable dosage of 0.1 to 1,000 mg/kg body weight daily for an adult.

EXAMPLES

The present invention will be explained below more specifically based on the examples. However, the scope of the present invention is not necessarily limited to the examples described below.

EXAMPLE 1

(1) Preparation of the Present Substance

A mixture of 100 g of a wheat bran commercially available and 3 l of water was placed in an autoclave and heated at 190° C. for 20 minutes for extraction. The unextracted substance was filtered out, about 4 volumes of ethanol was added to one volume of the filtrate and the mixture was kept at least overnight in a dark and cool place, and obtained 22.5 g of polysaccharide precipitate. The precipitate, after being dissolved in water, was dialyzed in cold water for 3 days using a visking tube (manufactured by Union Carbide C/rp.), and freeze-dried to give 19.4 g of white dietary fiber being tasteless and odorless (the yield being 19.4%) [Sample 1].

Alternatively, only changing the extraction condition, another batch of dietary fibers were obtained. The extraction was performed at 180° C. for 20 minutes [Sample 2] and at 170° C. for 20 minutes [Sample 3]. The yield was 26.2% for the sample 2 and 27.5% for the sample 3.

(2) Preparation of the Present Substance

A mixture of 600 g of a wheat bran commercially available and 20 l of water was placed in an autoclave and heated at 180° C. for 15 minutes for extraction. The unextracted substance was filtered out by continuous centrifugation, the filtrate was passed through a column filled with activated carbon and alumina to remove low molecular weight substances and the resultant solution was passed through an ultrafiltration membrane (BIFU-T2/A manufactured by PCI C/.) to obtain components having a molecular weight not lower than 5,000. The filtrate was freeze-dried and obtained 150 g of white dietary fiber being tasteless and odorless (the yield being 25%) [Sample 4].

COMPARISON EXAMPLE 1

A mixture of 100 g of a wheat bran commercially available and 3 l of water was placed in an autoclave and heated at 160° C. for 20 minutes. The extracted solution was treated in the same manner as Example 1 and obtained 30.5 g of dietary fiber [Sample 5].
Alternatively, only changing the extraction condition, dietary fiber was obtained. The extraction was performed at 150° C. for 20 minutes [Sample 6] and at 140° C. for 20 minutes [Sample 7]. The yield was 28.5% for the sample 6 and 26.4% for the sample 7. In addition, the extraction was performed at 100° C. for 20 minutes and obtained a dietary fiber [Sample 8].

EXAMPLE 2

The dietary fiber, samples 1 to 7, obtained in Example 1 and C/mparative Example 1 was analyzed to obtain the following data.

(1) Molecular Weight

With Waters gas permeable chromatography, as one of GPC-Lalls method, the molecular weight of solute and content of its fractions were calculated from its scattering intensity difference and refractive index difference of light passed through the solution dissolving the molecular chain of the sample and divided in size. Calculated molecular weight was the weight average molecular weight.

(2) Infrared Absorption Spectrum

The infrared absorption photometry of the samples was taken with a spectrophotometer (A-202, manufactured by NIHON BUNKO C/.) using the KBr tablet method. Among the spectra of the samples 1 to 7, a spectrum of the sample 2 is shown in FIG. 1 as representative.

(3) Optical Rotation

An aqueous solution containing 0.25% present substance (samples 1 to 7) was subjected to a polarimetric analysis with an automatic spectropolarimeter (DIP-360, manufactured by IHON BUNKO Co.) and determined the specific rotations of the samples.

(4) Sugar content

The sugar content of the present substance calculated as glucose was determined based on a color reaction of the phenol-sulfuric acid method with a spectrophotometer in a range of ultraviolet to visible light (UV-160A; manufactured by SHIMAZU SEISAKUSHO).

(5) Protein C/ntent

The protein content of the present substance calculated as bovine serum albumin was determined based on color reaction of the Lowry-F/lin method with a spectrophotometer in a range of ultraviolet to visible light (UV-160A).

(6) Elementary Analysis

A decomposed gas from the present substance was analyzed with a TCD detector in an automatic elementary analyzer (MT3; manufactured by YANAGIMOTO SEISAKUSHO).

(7) Solubility

The solubility was measured according to the description in the Japan Pharmacopoeia. The present substance is readily soluble in water but hardly soluble in chloroform, benzene, ethanol and ether.

(8) C/mposition of the Sugar C/mponents

The sugar components of the present substance were separated with an anion exchange resin in Bio-Liquid Chromatography (Bio-LC; manufactured by DIONEX C/.) and its composition was identified by a pulsed-and-metric method.

(9) C/mposition of the Amino Acid Components

The present substance, after being hydrolyzed, was analyzed with an amino acid analyzer (073 Type; HITACHI SEISAKUSHO), to give the amino acid composition.

(10) Enzymatic Analysis

The present substance was hydrolyzed and the molar ratio between $\alpha$- and $\beta$-glucoses was determined with $\alpha$-1,4- and $\beta$-1,4-glucosidases to have a ratio between $\alpha$- and $\beta$-glucose bonds.

(11) Sugar Bond

The present substance was, after methylation, hydrolyzed, and the resultant partially methylated sugars were acetylated and analyzed with a gas chromatograph (GC-14A; manufactured by SHIMAZU SEISAKU-SHO) and a mass spectrometer (JMS DX-303, NIHON DENSHI C/.), thereby we obtained identification and determination of the methylated sugar.

(12) Melting Point

The melting point of the present substance was measured by the DSC (Differential Scanning Calorimeter) method, however all the samples did not show a clear melting point but turned black at around 250° C. and carbonized.

The results of the samples 1 to 7 obtained by the above analytical methods given Table 2.

(13) Analysis of Dietary Fibers by Southgate Method

The content of water soluble and hardly digestible polysaccharide, cellulose, hemicellulose and lignin in the present substance was determined by the Southgate method, as follows:

To heated 85% ethanol, 100 g of each of samples 1 to 7 was placed to remove free sugar, and the solution was placed in a centrifuging tube of 50 ml capacity. A 60 ml of distilled water was added to the solution, and the mixture was heated in a boiling water bath to make the contained starch pasty and after, 0.3 ml of 2M acetic acid salt buffer solution (pH 4.6) and 1.5 ml of 10% takadiastase solution were added and the mixture was maintained at 37° C. for 18 hours to decompose starch. Then, 30 ml of ethanol was added to the solution, and the mixture was placed overnight in a cool place and centrifuged to remove glucose derived from starch. The remaining solution was dried and yielded about 30 g of high molecular weight dietary fiber which was hardly digestible.

Then, to 100 mg of the hardly digestible dietary fiber obtained by the enzymatic treatment, 3 ml of distilled water was added and the mixture was heated on a boiling water bath to remove ethanol. To the obtained solution 10 ml of heated distilled water was further added and the mixture was heated for 20 minutes on a boiling water bath and centrifuged to divide into two fractions, that are, a solution containing a hot water soluble substance and a solid which is insoluble in hot water. The former fraction contained the water soluble and hardly digestible polysaccharide and the latter fraction contained hemicellulose, cellulose and lignin. The hot water soluble fraction was cooled, 4 volumes of ethanol were added to one volume of the fraction and the mixture was centrifuged. 10 ml of 1sulfuric acid was added to the residue thus centrifuged and the mixture was heated at 100° C. for 2.5 hours. The hydrolyzed product was analyzed by the phenol-sulfuric acid method and determined the water soluble and hardly digestible polysaccharide.

Then, to isolate hemicellulose from the mixture of hemicellulose, cellulose and lignin in the hot water insoluble fraction, 10 ml of 1N sulfuric acid was added to the fraction in a centrifuging tube. The mixture was heated at 100° C. for 2.5 hours for hydrolysis and centrifuged. The supernatant of the fraction soluble to a diluted acid was used to determine the water insoluble hemicellulose component.

To the residue obtained by removing the dilute acid tained, while when the temperature is lower than 160° C., a dietary fiber largely composed of hemicellulose is obtained.

TABLE 1

| Number | Conditions of Extraction | | Yield of Dietary Fiber (%) | Analytical Result of Dietary Fiber by Southgate Method (%) | | | |
|---|---|---|---|---|---|---|---|
| | Temp. (°C.) | Time (Minute) | | Polysaccharide *1) | Cellulose | Hemicellulose | Lignin |
| Example 1 | 190 | 20 | 19.4 | 94.4 | 1.6 | 1.8 | 2.2 |
| Example 2 | 180 | 20 | 26.2 | 92.8 | 1.7 | 3.2 | 2.3 |
| Example 3 | 170 | 20 | 27.5 | 78.2 | 4.1 | 14.8 | 2.9 |
| Example 4 | 180 | 15 | 25.0 | 84.3 | 4.6 | 8.5 | 2.6 |
| Com. Ex. 1 *2) | 160 | 20 | 30.5 | 23.6 | 14.2 | 59.5 | 2.7 |
| Com. Ex. 2 *2) | 150 | 20 | 28.5 | 22.5 | 15.9 | 58.1 | 3.5 |
| Com. Ex. 3 *2) | 140 | 20 | 26.4 | 21.6 | 19.3 | 55.2 | 3.9 |

*1) This polysaccharide means a water-soluble polysaccharide which is hardly digestible.
*2) Com. Ex. means Comparative Example.

TABLE 2-I

| No. *4) | IR Absorption | | $[\alpha]_D^{25}$ *1) | Elementary Analysis | | | Amount of Sugar *2) (weight %) | Amount of Protein *3) (weight %) | Molecular Weight |
|---|---|---|---|---|---|---|---|---|---|
| | 3300 cm$^{-1}$ | 1650 cm$^{-1}$ | | C (%) | H (%) | N (%) | | | |
| Exam. 1 | + | + | +141° | 35.4 | 5.6 | 0.2 | 99.0 | 0.5 | 18,000 |
| Exam. 2 | + | + | +142° | 37.3 | 5.7 | 0.3 | 96.8 | 1.8 | 23,000 |
| Exam. 3 | + | + | +143° | 36.8 | 5.7 | 0.6 | 96.8 | 2.2 | 84,000 |
| Exam. 4 | + | + | +144° | 36.2 | 5.5 | 0.6 | 97.0 | 2.0 | 38,000 |
| Com. Ex. 1 | + | + | +147° | 35.0 | 6.8 | 1.6 | 95.0 | 3.1 | ≧100,000 |
| Com. Ex. 2 | + | + | +146° | 34.4 | 6.7 | 2.2 | 94.4 | 3.3 | ≧100,000 |
| Com. Ex. 3 | + | + | +146° | 32.8 | 6.8 | 2.1 | 94.4 | 3.4 | ≧100,000 |

*1) Specific rotatory power measured at C = 0.25, H$_2$O
*2) Measured with phenol-sulfuric acid method
*3) Measured with Lowry-Folin method
*4) Exam. means Example and Com. Ex. means Comparative Example soluble fraction, 10 ml of cold 72% sulfuric acid was added and the mixture was left to stand at 4° C. for 48 hours. The mixture was filtered under reduced pressure through a glass fiber filter placed on a Gooch crucible. The filtrate, the fraction soluble in cold 72% sulfuric acid, was used to determine the cellulose component.

The residue in the Gooch crucible was incinerated by heating at 500° C. for 3 hours. The weight of residue subtracted by an ash weight was taken as the lignin content.

Weights of the water soluble and hardly digestible polysaccharide, hemicellulose, cellulose and lignin under variable extracting conditions are summarized in Table 1. As is indicated in the table, when the extraction temperature is 170° C. or higher, the dietary fiber having the polysaccharide as the main component is obtained.

TABLE 2-II

| Number | Sugar Constituent (Mol %) | | | | | α-Binding β-Binding in Molar Ratio of Glucose Binding |
|---|---|---|---|---|---|---|
| | Glucose | Xylose | Galactose | Arabinose | Fucose | |
| Exam. 1 | 94.0 | 5.6 | 0.2 | 0.1 | 0.1 | 1/80 |
| Exam. 2 | 92.3 | 7.3 | 0.2 | 0.1 | 0.1 | 1/50 |
| Exam. 3 | 89.4 | 7.7 | 1.0 | 1.0 | 0.9 | 1/40 |
| Exam. 4 | 90.1 | 7.5 | 1.2 | 0.8 | 0.4 | 1/50 |
| Com. Ex. 1 | 87.7 | 8.8 | 1.3 | 1.1 | 1.1 | 1/30 |
| Com. Ex. 2 | 85.3 | 11.2 | 1.3 | 1.1 | 1.1 | 1/20 |
| Com. Ex. 3 | 82.8 | 13.7 | 1.3 | 1.1 | 1.1 | 1/20 |

TABLE 2-III

| No. | Amino Acid Constitution (Mol %) | | | | | | | | | | | | | | | |
|---|---|---|---|---|---|---|---|---|---|---|---|---|---|---|---|---|
| | Asp | Thr | Ser | Glu | Pro | Gly | Ala | Cys | Val | Ile | Leu | Tyr | Phe | Hyl | Lys | His | Arg |
| Exam. 1 | 2.7 | 2.9 | 7.2 | 32.7 | 10.4 | 13.2 | 7.2 | 0.2 | 4.2 | 3.6 | 4.6 | 1.8 | 3.8 | 1.9 | 1.8 | 1.4 | 0.4 |
| Exam. 2 | 2.9 | 3.7 | 7.7 | 30.1 | 10.8 | 13.7 | 7.6 | 0.1 | 4.7 | 3;2 | 5.4 | 1.5 | 3.8 | 1.5 | 1.4 | 1.2 | 0.7 |
| Exam. 3 | 4.2 | 3.7 | 7.2 | 31.2 | 10.6 | 13.4 | 7.4 | 0.1 | 4.0 | 3;0 | 5.5 | 1.3 | 3.3 | 0.9 | 1.5 | 1.5 | 1.2 |
| Exam. 4 | 3.5 | 4.0 | 7.5 | 29.7 | 10.2 | 12.8 | 8.0 | 0.1 | 4.4 | 3.4 | 5.2 | 2.0 | 3.5 | 1.2 | 1.5 | 1.2 | 1.8 |
| Com. Ex. 1 | 4.9 | 4.1 | 5.1 | 33.3 | 12.9 | 10.7 | 8.9 | 0.4 | 2.5 | 2.3 | 5.9 | 1.0 | 2.5 | 0.4 | 1.2 | 2.0 | 1.9 |
| Com. Ex. 2 | 4.9 | 4.1 | 5.0 | 33.8 | 12.9 | 9.5 | 8.9 | 0.4 | 2.6 | 2.2 | 6.0 | 1.0 | 2.2 | 0.8 | 1.2 | 2.1 | 2.4 |
| Com. Ex. 3 | 5.0 | 4.2 | 5.8 | 33.7 | 13.0 | 8.3 | 9.0 | 0.4 | 2;8 | 2.4 | 5.9 | 1.1 | 2.3 | 0.8 | 1.1 | 2.0 | 2.2 |

Asp = Aspargic acid; Thr = threonine; Ser = serine; Glu = glutamic acid; Pro = proline; Gly = glycine; Ala = alanine; Cys = cystine; Val = valine; Ile = isoleucine; Leu = leucine; Tyr = tyrosine; Phe = phenylalanine Hyl = hydroxylsine; Lys = lysine; His = histidine; Arg = arginine

TABLE 2-IV

| Number | Methylated Sugar Content (Mol %) *1) | | | | | |
|---|---|---|---|---|---|---|
| | 2,3,4,6-(CH$_3$)$_4$—GLC | 2,4,6-(CH$_3$)$_3$—GLC | 2,3,6-(CH$_3$)$_3$—GLC | 2,6-(CH$_3$)$_2$—GLC | 3,6-(CH$_3$)$_2$—GLC | 2,3-(CH$_3$)$_2$—GLC |
| Exam. 1 | 1.0 | 0.60 | 8.52 | 0.16 | 0.04 | 0.58 |
| Exam. 2 | 1.0 | 0.62 | 11.96 | 0.22 | 0.08 | 0.68 |
| Exam. 3 | 1.0 | 0.58 | 13.12 | 0.29 | 0.09 | 0.62 |
| Exam. 4 | 1.0 | 0.60 | 10.08 | 0.27 | 0.07 | 0.62 |
| Com. Ex. 1 | 1.0 | 0.54 | 18.42 | 0.34 | 0.12 | 0.71 |
| Com. Ex. 2 | 1.0 | 0.52 | 22.14 | 0.36 | 0.13 | 0.74 |

TABLE 2-IV-continued

| Number | Methylated Sugar Content (Mol %) *1) | | | | | |
|---|---|---|---|---|---|---|
| | 2,3,4,6-(CH₃)₄—GLC | 2,4,6-(CH₃)₃—GLC | 2,3,6-(CH₃)₃—GLC | 2,6-(CH₃)₂—GLC | 3,6-(CH₃)₂—GLC | 2,3-(CH₃)₂—GLC |
| Com. Ex. 3 | 1.0 | 0.52 | 25.35 | 0.36 | 0.12 | 0.72 |

*1) GLC means glucose.

As is apparent from Tables 1 and 2, the dietary fiber of the present invention is clearly different from the fiber extracted by water at a temperature below 160° C.

EXAMPLE 3

To a group of ICR-JCL mice (8 mice/group) subcutaneously transplanted with $10^6$ Sarcoma-180, the present substance (sample 2) dissolved in 0.1% physiological saline solution was intraperitoneally injected with a dosage amount of 10 mg/kg body weight 10 times every other day starting from 2 days after the transplantation. Two days after the completion of the injection, the tumors were weighed. The control mice were injected with only physiological saline and their tumors were also weighed in the same manner. From these results, the inhibitory effect on tumor growth was calculated from the following equation and the result is shown in Table 3.

$$I.R. (\%) = \left[ \frac{\text{Average Tumor weight of Control Group} - \text{Average Tumor weight of Testing Group}}{\text{Averge Tumor weight of Control Group}} \right] \times 100.$$

TABLE 3

Antitumor Activity of the Present Substance

| Sample | Average Weight of Tumor (mg) (X ± S.D.) | Inhibiting Ratio I.R. (%) |
|---|---|---|
| Present Substance (Sample No. 2) | 797.5 ± 755.8 | 84.9 |
| Control | 5,282.2 ± 6,849.4 | — |

EXAMPLE 4

Aqueous solutions 5% of the present substances prepared in Example 1 were prepared and a 5% aqueous solution of fructo-oligosaccharide commercially available was also prepared as a comparison.

The above preparations are given forcibly orally to groups (10 mice/group; 3 groups) of C₃H/He female mice (8 weeks of age) at a daily dose of 0.5 g/kg body weight, as a solid, for 21 days.

F/r the control group, a same amount of physiological saline was forcibly given orally to mice for the same period. Before and after the tests, feces of the mice under study were collected. The feces were put into 100 volumes of anerobic diluting solution (phosphate buffer) and milled the feces to powder. An aliquot (0.1 ml) of these mixtures were respectively coated on a surface of B.S medium and incubated anerobically (an anaerobic glove box method) at 37° C. for 1 to 5 days. After the cultivations was over, number of *Lactobacillus bifidus* on each medium was counted. The results are shown in Table 4. Each figure in the table indicates an average number obtained from ten animals.

TABLE 4

Growth Rate of Lactobacillus bifidus by the Present Substance

| | No. of the Bacterium/g of Feces | | |
|---|---|---|---|
| Sample | Before Administration (A) | 21st Day After Administration (B) | (B)/(A) |
| Sample 2 | $3.8 \times 10^4$ | $4.6 \times 10^5$ | 12.1 |
| Sample 1 | $3.8 \times 10^4$ | $5.1 \times 10^5$ | 13.4 |
| Sample 3 | $3.8 \times 10^4$ | $4.8 \times 10^5$ | 12.6 |
| Fructo-oligosaccharide | $3.9 \times 10^4$ | $3.9 \times 10^4$ | 1.0 |
| Control | $4.1 \times 10^4$ | $3.7 \times 10^4$ | 0.9 |

EXAMPLE 5

C₃H/He mice in four groups (28 mice/group) were freely given a feed which induce in mouse hypercholesterolemia experimentally and at the same time the present substance prepared in Example 1 orally at a dose of 500 mg/kg body weight daily.

Mice in the control group were forced to take orally 500 mg/kg of physiological saline daily instead of the present substance. The result is given in Table 5. The result indicates that the present substance significantly reduces accumulation of cholesterol in the blood and liver.

TABLE 5

Reducing Effect on Cholesterol Accumulation

| | Cholesterol Content (mg/ml) | |
|---|---|---|
| Sample | In Blood | In Liver |
| Present Substance (Sample 2) | 135 | 38.3 |
| Present Substance (Sample 1) | 130 | 37.4 |
| Present Substance (Sample 3) | 140 | 40.4 |
| Control | 167 | 58.1 |

EXAMPLE 6

Phytohemagglutinin, which is a representative mitogens, and chlorambucil (hereinafter referred to as "CBL"), which is a lymphocyte suppressor of and is an antitumor agent, were allowed to act upon monocytes (a type of lymphocytes) obtained from human peripheral blood. At the same time, the present substances prepared in Example 1 and dietary fibers prepared in C/mparative Example 1 were respectively given in an amount of $10^{-2}$ μg to each of the above mixture. After incubation of a certain period, the uptakes of ³H-thymidine by lymphocytes were determined and the effect of the present substance on the human lymphocytes were evaluated.

As a positive control, lentinan, an antitumor agent used in an immunological therapy, was used instead of dietary fibers. The result is given in Table 6.

The result indicates that the present substance is effective in restoring the activity of human lymphocytes 7hich has been significantly suppressed, while dietary fiber prepared with an extraction at a temperature below 160° C. does not show the effect.

TABLE 6

Relation between Extraction Temperature and Immunology Activation (in vitro)

| Sample | Blastogenesis of Monocyte | |
|---|---|---|
| | Uptake of $^3$H-Thymidine (cpm) | Activity |
| Present Substance (Sample 2) + CBL 2.5 μg/ml | 138,775 ± 12,700** | ○ |
| Present Substance (Sample 1) + CBL 2.5 μg/ml | 148,775 ± 12,700** | ○ |
| Present Substance (Sample 3) + CBL 2.5 μg/ml | 135,226 ± 10,883** | ○ |
| Comparative Example (Sample 5) + CBL 2.5 μg/ml | 92,175 ± 6,802 | X |
| Comparative Example (Sample 7) + CBL 2.5 μg/ml | 73,901 ± 2,351 | X |
| Comparative Example (Sample 8) + CBL 2.5 μg/ml | 91,865 ± 2,157 | X |
| Lentinan | 93,620 ± 6,651 | X |
| Control | 88,832 ± 12,700 | — |

**: $p < 0.01$
○: Active
X: Inactive

EXAMPLE 7

Groups of 10 normal C57BL/6.J female mice were forced to take orally CBL at 10 mg/kg body weight and at the same time, the present substances prepared in Example 1 and dissolved in physiological saline at a dose of 250 mg/kg body weight were given freely for 5 days daily. After the tests were over, the spleen of each mouse was extirpated and number of lymphocytes in it was counted. Then, suspensions prepared at a concentration of $2.5 \times 10^6$ lymphocytes/ml were respectively placed on each well of a 96-well microplate with phytohemagglutinin and incubated for a certain period. After the incubation the uptake of $^3$H-thymidine by the lymphocyte was measured and the effect of an oral administration of the present substance on the splenic lymphocytes in mouse was studied.

To a control group, physiological saline without any dietary fiber was given freely and the effect on the splenic lymphocytes in mouse was studied in the same manner as above. The result is given in Table 7.

The result indicates that ingestion of the present substance is significantly effective even in recovering a significantly reduced activity of mouse splenic lymphocytes and in maintaining their blastomogenous activity.

TABLE 7

Effect of The Present Substance on Enhancing Immunological Response in Vivo

| Sample | No. of Lymphocytes in Spleen (No./mouse) | Uptake of $^3$H-thymidine (cpm) |
|---|---|---|
| Sample 2 | $4.0 \times 10^7$* | 38,496 ± 7,270* |
| Sample 1 | $4.2 \times 10^7$* | 40,775 ± 6,700* |
| Sample 4 | $4.1 \times 10^7$* | 35,226 ± 8,883* |
| Control | $2.6 \times 10^7$ | 23,514 ± 6,169 |

*: $P < 0.05$

EXAMPLE 8

To C$_3$H/He female mice aged 9 weeks and weighing 21 to 24 g, the present substance prepared in Example 1 was dissolved in water and orally given &/rcibly at a dose of 5 g/kg body weight and the states of the mice were observed for 3 weeks.

To a control group, only physiological saline was given. The results are given in Table 8. The results show that the groups treated with the present substance exhibit no abnormality and gave no death. Accordingly, it is demonstrated that the present substance is highly safe in use.

EXAMPLE 9

To 300 g of the present substance prepared in Example 1 (sample 2), 700 g of milk was added and after being boiled for pasteurization, was maintained at 43° C. On the other hand, to 20 g of milk which was maintained at 30° C. after being boiled for pasteurization, 2 g of an active lactobacillus containing *Lactobacillus bulgaricus* (manufactured by MEITO YUGYO, C/.) commercially available was added. The latter solution was added to the former solution containing the present substance and the mixture was maintained at 43° C. for 10 hours with a thermostat and obtained an edible product.

EXAMPLE 10

This example relates to one example of formulation of pharmaceutical composition of the present substance.

| | |
|---|---|
| The present substance (Sample 4) | 10 parts by weight |
| Heavy magnesium oxide | 15 parts by weight |
| Lactose | 75 parts by weight |

They were mixed uniformly and made powder or granule to give powdered drug. Further, the powder is put into capsules.

TABLE 8

Effect on Body Weight Change of the Present Substance

| Sample | Body Weight Before Test ($\bar{X}$ ± S.D.) | Body Weight After 3 Weeks ($\bar{X}$ ± S.D.) |
|---|---|---|
| Sample 2 | 20.7 ± 0.09 | 23.7 ± 0.49 |
| Sample 1 | 20.7 ± 0.95 | 23.4 ± 0.49 |
| Sample 3 | 20.8 ± 0.97 | 23.6 ± 0.50 |
| Control | 20.8 ± 0.75 | 23.1 ± 0.66 |

What is claimed is:

1. A dietary fiber which is obtained by a process comprising the steps of:
   (i) extracting, at least once, wheat bran with water at a temperature of 180° to 200° C., (ii) filtering and removing insoluble substances from the extracted solution, (iii) purifying the extracted solution by salting-out, dialysis, ultrafiltration, reverse osmosis, gel filtration or precipitation to remove substances having molecular weight not higher than 400, and (iv) freeze-drying the purified solution to obtain a solid dietary fiber, the resulting dietary fiber having the following properties:
   (a) an average molecular weight of $5 \times 10^2$ to $1 \times 10^5$ measured by a GPC-Lalls method;
   (b) a sugar content, determined by a color reaction of the phenol-sulfuric acid method, of 95.3 to 99.0% by weight and a protein content, determined by a color reaction of the Lowry-Folin method, of 0.1 to 3.0% by weight;

(c) contains 88.2 to 95.4 mol % glucose, 3.7 to 7.7 mol % xylose, 0.1 to 1.2 mol % galactose, 1.0 mol % or less fructose and 1.1 mol % or less arabinose;

(d) contains at least one amino acid selected from the group consisting of aspartic acid, threonine, serine, glutamic acid, proline, glycine, alanine, cysteine, valine, isoleucine, leucine, tyrosine, phenylalanine, hydroxylsine, lysine, histidine, and arginine;

(e) a molecular ratio between $\alpha$-bound glucose and $\beta$-bound glucose in a glucose component of 1:40 to 1:80;

(f) a molar concentration of 1,4-glucose bond is 85 to 90% and a molar concentration of 1,3-glucose bond is 4 to 10%; and (g) an analytical result of a sugar component thereof by the Southgate method is:

|  | % by weight |
|---|---|
| water soluble and hardly digestible polysaccharides | 78 to 96 |
| cellulose | 1.0 to 5.7 |
| hemicellulose | 1.7 to 15 |
| lignin | 1.3 to 3.3. |

2. A foodstuff containing the dietary fiber of claim 1.

3. The foodstuff according to claim 2 wherein the foodstuff is a beverage.

4. A dietary composition containing the dietary fiber defined in claim 1 together with a carrier or diluent.

5. A pharmaceutical composition comprising the dietary fiber defined in claim 1 together with a pharmaceutically acceptable carrier or diluent.

* * * * *